| United States Patent [19] | [11] | 4,178,265 |
|---|---|---|
| Matsuda et al. | [45] | Dec. 11, 1979 |

[54] OIL COAGULANT AND PROCESS FOR PREPARATION THEREOF

[75] Inventors: Yoshindo Matsuda; Shigeru Tomita, both of Tokyo; Keiji Abe, Higashi-Kurume; Kazuki Terajima, Tokyo, all of Japan

[73] Assignee: Agency of Industrial Science & Technology, Tokyo, Japan

[21] Appl. No.: 880,278

[22] Filed: Feb. 22, 1978

[30] Foreign Application Priority Data

Feb. 24, 1977 [JP] Japan .................. 52-19440

[51] Int. Cl.$^2$ ............... B01J 13/00; B01D 17/02; C02B 1/20
[52] U.S. Cl. .................... 252/316; 210/59; 210/DIG. 27; 252/358
[58] Field of Search ................ 252/316, 358; 210/DIG. 27, 59; 195/57, 60

[56] References Cited

U.S. PATENT DOCUMENTS

| 3,755,189 | 8/1973 | Gilchrist et al. ............ 252/316 |
| 3,821,109 | 6/1974 | Gilchrist et al. ............ 210/DIG. 27 |
| 3,856,667 | 12/1974 | Azarowicz .................. 210/DIG. 27 |

FOREIGN PATENT DOCUMENTS 51-41597  11/1976  Japan .................. 210/DIG. 27

*Primary Examiner*—Richard D. Lovering
*Attorney, Agent, or Firm*—Armstrong, Nikaido, Marmelstein & Kobovcik

[57] ABSTRACT

A mixture of a carboxymethylated yeast with a higher fatty acid and the like is prepared, and a water-soluble polyvalent metal salt of an inorganic acid is added to the mixture in the presence of water. The resulting composition has an oil-coagulating effect.

29 Claims, No Drawings

OIL COAGULANT AND PROCESS FOR PREPARATION THEREOF

BACKGROUND OF THE INVENTION

The present invention relates to a coagulant for oils, especially oils spilled on the water surfaces of seas, harbours, rivers, lakes, swamps and the like, and also to a process for the preparation of such oil coagulant.

Recently, occurrence of accidents of outflow of crude oil and refined oil into seas, harbours, rivers, lakes, swamps and the like becomes intensive with developments in excavation of oil wells, transportation of crude oils and petrochemical industries. Oil spill into seas or the like results in occurrence of fires and pollution of seas. Accordingly, attempts have been made to prevent expansion of spilled oils in seas or the like by using oil treating agents, for example, oil coagulants.

Oil treating agents that are now used to cope with accidents of oil spills are emulsifiers having a function of dispersing spilled oils into sea water. These agents do not remove oils acting as the contamination sources and there is involved a risk that toxicities of these agents have bad influences on marine products. Accordingly, inhibition of use of these oil treating agents is now demanded, and the Transport Ministry of the Japanese Government has issued an official notice inhibiting use of oil treating agents having an emulsifying action "unless fires and other accidents causing a loss of lives or a serious damage of property occur or there is a risk of occurrence of such accidents".

Under such background, it has been eagerly desired to develop and use an oil treating agent having novel characteristics, namely an oil treating agent which can be used instead of the conventional oil treating agents for prevention occurrence of fires when oils spill and which has no bad influences on marine products and enables recovery of oils acting as contamination sources.

As an oil treating agent meeting such desire, we have already developed and published a protein type spilled oil treating agent (Japanese Pat. No. 822,527). This oil treating agent has a considerable effect but it leaves much room for improvement in properties thereof. For example, when this treating agent is sprinkled on the water surface on which an oil flows out, the water layer is made turbid more or less by application of the agent, though the oil is coagulated in the gel-like form to prevent occurrence of a fire or expansion of the oil and facilitate recovery of the oil and the agent has other characteristic properties such as the absence of any toxicity. Of course, this turbidity-causing component is quite harmless and has no bad influences on marine products. However, elimination of this action of rendering water turbid is desired. Accordingly, it is eagerly desired to develop an oil coagulant which does not render water turbid or show any emulsifying action when applied to the water surface, and which can coagulate a spilled oil completely and can be prepared very easily.

As a result of our researches made with a view to developing such oil coagulant and establishing a process for the preparation thereof, we have now completed the present invention.

OBJECT OF THE INVENTION

It is a primary object of the present invention to provide a novel oil coagulant and a process for the preparation thereof.

Another object of the present invention is to provide an oil coagulant having a high oil-coagulating activity and a process for preparing this oil coagulant very easily.

Other objects and advantages of the present invention will be apparent from the description given hereinafter.

BRIEF SUMMARY OF THE INVENTION

In accordance with the present invention, the foregoing objects can be attained by an oil coagulant composed of a composition comprising 100 parts by weight of a carboxymethylated yeast and, incorporated therein, 10 to 150 parts by weight of a polyvalent metal salt of at least one member selected from higher fatty acids and alicyclic carboxylic acids.

This composition acting as an oil coagulant is prepared according to a process comprising carboxymethylating a yeast and mixing 100 parts by weight of the resulting carboxymethylated yeast with 10 to 150 parts by weight of a polyvalent metal salt of at least one member selected from higher fatty acids and alicyclic carboxylic acids.

DETAILED DESCRIPTION OF THE PREFERRED EMBODIMENTS

An oil coagulant of the present invention, a process for the preparation thereof and characteristic properties of the oil coagulant will now be described in detail.

The yeast and other starting materials necessary for preparation of the oil coagulant of the present invention is first described.

Substantially all the kinds of yeasts can be effectively used in the present invention. For example, there can be used yeasts cultured by using normal paraffin, natural gas, molasses, pulping waste liquor, methanol, ethanol, acetic acid, glucose or the like as a carbon source. In other words, there can be used yeasts belong to the genera *Candida, Torulopsis, Hansenula, Saccharomyces* and *Torula.* In addition to these yeasts, there can be similarly employed cells of bacteria, for example, those belonging to the genera *Pseudomonas, Corynebacterium, Bacillus, Methanomonas* and *Aerobacter.* However, cells of bacteria are fine in size and industrial production and handling of such cells involve difficulties. Accordingly, cells of yeasts are preferably employed as the cells in the present invention. Cells of either dry yeasts or living yeasts may be used in the present invention, and mixtures of two or more kinds of yeasts may be used. As examples of yeasts that can be preferably employed, there can be mentioned yeasts belonging to the genus *Candida,* such as *Candida utilis, Candida tropicalis* and *Candida lipolytica,* which have been cultured by using a hydrocarbon such as normal paraffin as a carbon source, yeasts belonging to the genus *Saccharomyces,* such as *Saccharomyces cerevisiae,* which have been cultured by using molasses as a carbon source, and yeasts belonging to the genus *Torula,* such as *Torula utilis,* which have been cultured by using pulping waste liquor as a nutrient.

In the present invention, a yeast such as mentioned above is used in the carboxymethylated form. Carboxymethylation can be accomplished by reacting the yeast with monochloroacetic acid or an alkali metal salt thereof. At this carboxymethylation step, active hydrogen atoms of carbohydrates or proteins including the yeast react with monochloroacetic acid to effect carboxymethylation. Reaction conditions for this carboxymethylation will now be described in detail.

The starting yeast may be wet or dry. When a wet yeast is used, it is preferred that the water content be reduced below 50% and the water content be actually measured in advance. At first, water is added to the yeast in an amount of 0 to 1.9 Kg per Kg of the dry weight of the yeast, and 450 to 3600 g of a 40% by weight aqueous solution of sodium monochloroacetate is added to the mixture. Then the mixture is sufficiently kneaded for 0.5 to 3 hours. After the kneading operation, 93 to 742 ml of a 45% by weight aqueous solution of NaOH is added to the mixture under sufficient stirring over a period of at least 30 minutes. After completion of the alkali, the mixture is kneaded for 0.5 to 10 hours. For this reaction, the temperature is maintained at 5° to 60° C., preferably 30° to 50° C. In this carboxymethylation process, the order of addition of sodium monochloroacetate and the alkali may be reversed, and the molar ratio of NaOH to sodium monochloroacetate need not be controlled precisely to 1 but may be adjusted in the range of from 1.1 to 8.

Monochloroacetic acid per se may be used instead of sodium monochloroacetate. In this case, the amounts added of the acid and alkali should be adjusted appropriately based on the above-mentioned recipe.

In the present invention, it is preferred that water be present in the reaction mixture in an amount of 1.6 to 2.8 Kg per Kg of the dry yeast for the above reaction.

The main reaction of carboxymethylation is completed according to the above procedures. In many cases, it is preferred to subject the resulting carboxymethylated yeast to a heat treatment. More specifically, the reaction mixture is heat-treated after or without addition of water. The heat treatment conditions are changed depending on the carboxymethylation reaction conditions, but in general, the heat treatment is carried out at about 50 to about 90° C. for 0.5 to 5 hours.

As the second starting material, there is used a higher fatty acid, an alicyclic carboxylic and/or a metal salt thereof. More specifically, saturated or unsaturated linear fatty acids having 8 to 22 carbon atoms are used as the higher fatty acid, and as specific examples, there can be mentioned lauric acid, myristic acid, palmitic acid, behenic acid, stearic acid and mixtures of these fatty acids. In the present invention, stearic acid is especially preferred among these fatty acids. As the alicyclic carboxylic acid, there can be used naphthenic acids, resin acids and rosin acids having 8 to 22 carbon atoms, and use of naphthenic acids and rosin acids is preferred in the present invention. These acids may be used in the form of a metal salt. However, in a preferred embodiment of the present invention described hereinafter, where the acid component is mixed with a water-soluble polyvalent metal salt of an inorganic acid in the presence of water, the acid component need not be particularly used in the form of a metal salt. However, if the acid component is used in the form of a metal salt, it is necessary that a salt of a metal different from the metal of the above-mentioned water-soluble salt, for example, an alkali metal salt or ammonium salt, should be used. The metal of the metal salt of the carboxylic acid is generally selected from Mg, Ca, Ba, Al, Cu, Ni, Co, Mn, Zn, Pb, Cd, Ti, Cr. Fe, Ce and Zr. When a naphthenic acid salt is used, Co, Pb, Mn, Ca, Al, Zn, Zr, Cu and Fe are preferred as the metal component, and use of mixtures of salts of two or more of these metals is especially preferred. Among mixtures of metal salts, there are preferably employed mixtures of two or more of Ca, Mg, Al and Fe salts, especially mixtures of Al salts with one or more of Ca, Mg and Fe salts.

As the water-soluble polyvalent metal of an inorganic acid that is mixed with the higher fatty acid or the like in the presence of water, there can be mentioned Mg, Ca, Ba, Al, Cu, Ni, Co, Mn, Zn, Pb, Ti, Cr, Fe, Ce and Zr salts of sulfuric acid, hydrochloric acid and nitric acid. Especially preferred salts include $Al_2(SO_4)_3$, $AlCl_3$, $AlK(SO_4)_2$, $AlNH_4(SO_4)_2$, $Fe_2(SO_4)_3$, $FeCl_3$ and $CaCl_2$.

The carboxymethylated yeast is mixed with a carboxylic acid salt such as mentioned above, or the carboxymethylated yeast is first mixed with a carboxylic acid such as mentioned above and then mixed with a water-soluble polyvalent metal salt of an inorganic acid such as mentioned above in the presence of water. In the latter case, it is preferred to use the carboxylic acid in the state dissolved in a solvent. As the solvent, there can be used aqueous solutions of alkalis and water-miscible organic solvents such as alcohols and ketones, e.g., acetone. When the carboxylic acid or its salt is not dissolved in a solvent, the solvent may be added to the carboxymethylated yeast or simultaneously to the two starting materials.

In the above-mentioned operation, the mixing ratio of the carboxymethylated yeast and the polyvalent salt of the carboxylic acid is determined based on experiments so that the amount of the metal salt of the carboxylic acid in the final composition in the dry state is 8 to 140 parts by weight, preferably 30 to 100 parts by weight, per 100 parts by weight of the carboxymethylated yeast.

The fatty acid added to the carboxymethylated yeast is converted to a polyvalent metal salt at the subsequent step. More specifically, when a mixture of the carboxymethylated yeast and the above-mentioned carboxylic acid component is sufficiently mixed and kneaded with a water-soluble polyvalent metal salt in the presence of water, there is obtained a composition comprising a mixture of the carboxymethylated yeast and a polyvalent metal salt of the above-mentioned carboxylic acid.

Alternately, there may be adopted a method in which the carboxymethylated yeast is mixed with two compounds capable of forming the above-mentioned metal salt of the carboxylic acid by reaction, namely a higher fatty acid, an alicyclic carboxylic acid and/or a salt of such acid with an alkali metal, ammonium or organic base such as triethanolamine and a water-soluble polyvalent metal salt of an inorganic acid, according to procedures such as described above.

More specifically, according to this modification, the carboxymethylated yeast is mixed with a carboxylic acid component in the solid or solution state. When the carboxylic acid component is used in the free form, namely not as a salt, it is indispensable that a free alkaline substance should be present in the mixture in an amount larger than the amount necessary for neutralizing the carboxylic acid. Further, since the dependency of the water solubility of the carboxylic acid on the temperature is very high, it is necessary to effect heating sufficiently under stirring before or during addition. Then, the polyvalent metal salt is added in the solid state or in the form of an aqueous solution. When the polyvalent salt is added in the solid state, it is necessary that the reaction mixture should have such a water content that the added salt can be completely dissolved by water contained in the reaction mixture. It is preferred that the polyvalent metal salt be added in an amount of 1.5 to 15 moles per Kg of the crude carboxymethylation product. When the mixture is sufficiently stirred after addition of the polyvalent metal salt, the effective ingredient is separated in the solid or powdery form. Then, a suitable amount of an acid or alkali is added to adjust the pH to about 4.5 and the precipitate is separated by filtration or centrifugal separation. The recovered product is washed with water according to need and if desired, a hydroxide or carbonate of an appropriate alkali is added to the product to adjust the pH to the neutral value. The resulting product composition is separated from the water phase in the form of powder that can easily be filtered, and it can be separated from the supernatant by filtration or centrifugal separation to obtain the intended product. The product may be powdered by drying or it may be mixed with water to form a slurry.

The so obtained polyvalent metal salt-treated product of a mixture of the carboxymethylated yeast and the thickening assistant has a prominent effect of coagulating a spilled oil without pollution of water in the scattered area. More specifically, when this oil coagulant of the present invention is scattered on the water surface on which an oil flows out, the flow-out oil is converted to a hydrous gel having a viscosity of $10^4$ to $10^5$ cp, and in this case, the powdery coagulant does not migrate into the water phase. Accordingly, water pollution is not caused and there is not a fear or risk of occurrence of secondary pollution by pollution of water in the scattered area.

The process of the present invention has the following advantages.

When a yeast is carboxymethylated according to a customary technique, NaCl, a sodium salt of the acid used for neutralization and in some case, a sodium salt of glycolic acid are formed as by-products and therefore, purification is indispensable for removal of these by-products. Purification is usually performed by washing the carboxymethylation product with an alcohol containing 10 to 20% by volume of water. Therefore, even if carboxymethylation is carried out by the process using an aqueous medium, an organic solvent must be used for the purification and the advantage of the aqueous medium process, namely the low running cost, can be attained insufficiently. In contrast, the process of the present invention is characterized in that a polyvalent metal salt is finally added in the presence of water to precipitate the intended product, and therefore, by-products such as mentioned above are left in the supernatant and the effective ingredient alone can be recovered by filtration or centrifugal separation. Accordingly, purification using a water-containing alcohol need not be performed and the advantage of the aqueous medium process can be fully attained.

In the present invention, when a polyvalent metal salt is added and kneading is carried out, a polyvalent metal salt of the fatty acid is simultaneously formed and this salt has a function of promoting formation of the precipitate. Accordingly, as compared with the case where no fatty acid is present, formation of the precipitate can be accomplished more completely. Namely, when the carboxymethylated yeast is precipitated by using a polyvalent metal salt, the final pH of 4 to 5 is most preferred for precipitation, and a product obtained at this optimum pH is often inferior to a product obtained at other pH with respect to the capacity of coagulating fuel oil B. On the other hand, when a polyvalent metal salt of the fatty acid is present in the reaction mixture, since the precipitation is promoted, a product having a higher coagulating activity can be obtained sufficiently at a pH outside the above-mentioned optimum range. This is another advantage attained by the present invention. For the same reason, there can be attained still another advantage that the amount used of the polyvalent metal salt can be reduced.

The thickening effect of the product of the present invention for spilled oils is much higher than the thickening effect of a product obtained without addition of the carboxylic acid component as the thickening assistant, and the turbidity of water in the scattered area can be remarkably reduced. Further, since the polyvalent salt of the fatty acid is water-repellent, the product of the present invention containing this water-repellent salt is hardly soluble in water and has a property of readily rising on the water surface. Therefore, even if it is scattered on water in an oil-free area, it does not precipitate or disperse in water and there is hardly any possibility that the product of the present invention cause pollution of sea water. Still further, even if the specific gravity of the rising gel of the thickened oil is increased by evaporation of light oil components or the like, the possibility of submergence of the gel beneath the water surface can be completely eliminated. This is still another great advantage attained by the present invention.

The present invention will now be described in detail by reference to the following Examples that by no means limit the scope of the invention.

In these Examples, fuel oil was contacted and mixed with the coagulant and increase of the viscosity of the fuel oil, namely the thickening effect, was examined as a parameter indicating the oil-coagulating effect. This test for evaluating the effect of coagulating a spilled oil was carried out in the following manner.

A 1-liter capacity of a conical beaker was charged with 400 ml of distilled water or artificial sea water and 10 ml of fuel oil B was added thereto, and precisely measured 0.1 g of an oil coagulant sample was scattered on the content of the beaker. Then, the beaker was attached to a thermostat shaking device (shaking amplitude=9 cm; shaking frequency=80 strokes per minute) maintained at 25° C. and the mixture in the beaker was shaken for 1 to 2 hours. The viscosity of the obtained gelled fuel oil was measured at 25° C. by using an improved B-type viscometer.

EXAMPLE 1

To 100 g of dry cells of a yeast of the species *Candida utilis* was added 84.2 ml of water, and a solution of 0.617 mole of sodium monochloroacetate dissolved in 107.9 ml of water was added to the mixture. The resulting mixture was sufficiently kneaded in a kneader and 37 ml of a 45% aqueous solution of NaOH was gradually added to the mixture. After completion of the addition, the kneader was maintained at 40° C. and kneading was conducted for 2 hours to obtain a crude carboxymethylation product. Then, the temperature of the kneader was elevated to 70° C. and the reaction mixture was kneaded and heat-treated for 2 hours. Then, a portion (¾ of the total weight) of the product was withdrawn from the kneader, and a part of the withdrawn product was kept as it was and the remainder was dried. Separately, the remaining ¼ (92 as the wet product) of the product was mixed with a liquid mixture of 11.05 of stearic acid, 1.565 g of NaOH and 183.6 cc of water, and the mixture was sufficiently kneaded. Then, a solution formed by dissolving 30.81 g of aluminum sulfate in water in an amount 2 times the amount of aluminum sulfate was added to the mixture, and the mixture was sufficiently kneaded, withdrawn from the kneader and dried.

When the effect of increasing the viscosity of fuel oil B by the so obtained dried product was measured at 25° C., there was obtained a value of $7.7 \times 10^4$ cp.

For comparison, a known coagulant, "Diatreat" (sorbitolbenzaldehyde condensation product), was mixed with fuel oil B at a ratio of 15 g/100 ml and the thickening effect was measured after 20 hours. It was found that the viscosity was $76 \times 10^2$ cp.

EXAMPLE 2

Water was added to 25 g of a wet crude product obtained in the same manner as described in Example 1 except that *Candida lipolytica* was used as the dry yeast, to dissolve the crude product in water, and an aqueous solution of sodium stearate containing 0.6 g of stearic acid was added to the solution and the mixture was sufficiently blended. Then, an aqueous solution containing aluminum sulfate in an amount of 0.73 g as aluminum was added to the mixture and the pH was adjusted to 4.5 or 6 by sulfuric acid or sodium hydroxide. The resulting precipitates were dried to obtain samples A and B, and the thickening effects of these samples were determined according to the above-mentioned method to obtain results shown in Table 1.

Table 1

| Sample | pH | (Thickening Effects) Viscosity (cp) of Gelled Fuel Oil B |
|---|---|---|
| A | 4.5 | $8.9 \times 10^4$ |
| B | 6 | $9.3 \times 10^4$ |

EXAMPLE 3

Sample coagulants were prepared in the same manner as described in Example 2 except that 10 g of a dry crude product obtained by using *Saccharomyces cerevisiae* as the dry yeast was treated while changing the amounts of stearic acid and aluminum as indicated below. With respect to each of the so obtained samples, the thickening effect was determined to obtain results shown in Table 2.

Table 2

| Sample | Amount (g) of Stearic Acid | Amount (g) of Aluminum | pH | Viscosity (cp) of Gelled Fuel Oil B |
|---|---|---|---|---|
| C | 0 | 0.57 | 6 | $0.76 \times 10^4$ |
| D | 0.8 | 0.59 | 6 | $1.9 \times 10^4$ |
| E | 1.5 | 0.61 | 6 | $5.7 \times 10^4$ |

As will be apparent from the results shown in Table 2, the viscosity is enhanced with increase of the amount added of stearic acid, and the data prove the effect of the present invention. Further, a higher thickening effect can be obtained by the use of a coagulant from wet crude product than by the use of that from dry crude product, and it is seen that it is desired that the process for the preparation of a coagulant is conducted consistently and continuously from the carboxymethylation step.

EXAMPLE 4

In each of the foregoing Examples, the aqueous phase at the thickening effect test was completely colorless and transparent. Also in the case where the aluminum salt alone was added without addition of stearic acid, the aqueous phase was completely colorless and transparent. In contrast, in case of a sample formed without addition of aluminum, the aqueous phase at the thickening effect test was slightly turbid.

Accordingly, the thickening effects of a sample (sample F) prepared according to the method of Japanese Patent Application Laid-Open Specification No. 40489/75 and purified with methanol after carboxymethylation, a sample (sample G) prepared in the same manner as described in Example 3 except that 0.14 g of aluminum was added to 1 g of a crude carboxymethylated product without addition of stearic acid and the above-mentioned sample B were determined under the same conditions as described above except that the amount of the sample was changed to 0.2 g from 0.1 g. At predetermined intervals, the aqueous phase was sampled and the absorbances at 225 nm and 800 nm were measured by using a 100 mm quartz cell.

The absorption at 225 nm indicates mainly the presence of proteins and the absorption at 800 nm indicates the degree of the transparency of sample water. The absorbance at 225 nm was determined by adding 1N NaOH solution to sample water, the volume of added 1N NaOH solution being the same as the volume of sample water, adjusting the mixture to the colorimetric analysis and making calculation while amending the absorbance of 1N NaOH. Sample water in the as-collected state was used for the colorimetric analysis for determining the absorbance at 800 nm. Absorbances (O.D.) measured at predetermined intervals are shown in Table 3.

Table 3

(Results of Measurement of Absorbance of Aqueous Phase)

| Wavelength Time for Collection of Sample Water | Sample F | | Sample G | | Sample B | |
|---|---|---|---|---|---|---|
| | 225 nm | 800 nm | 225 nm | 800 nm | 225 nm | 800 nm |
| 0 minute | 0.7 | 0.045 | 0.38 | 0.003 | 0.39 | 0.002 |
| 5 minutes | 1.24 | 0.079 | 0.47 | 0.007 | 0.42 | 0.004 |
| 12 minutes | 1.26 | 0.064 | 0.52 | 0.003 | 0.42 | 0.003 |
| 30 minutes | 1.14 | 0.049 | 0.58 | 0.004 | 0.36 | 0.004 |
| 60 minutes | 1.31 | 0.083 | 0.57 | 0.006 | 0.34 | 0.006 |
| 90 minutes | 1.29 | 0.085 | 0.53 | 0.007 | 0.35 | 0.005 |
| 120 minutes | 1.18 | 0.084 | 0.50 | 0.006 | 0.33 | 0.006 |

As will readily be understood from the results shown in Table 3, the absorbance at 225 nm of the aluminum-treated product is ½ to ⅓ of the absorbance at 225 nm of the purified product, and the absorbance at 800 nm of the aluminum-treated product is about 1/10 of the absorbance at 800 nm of the purified product. Further, in case of the product of the present invention prepared by adding stearic acid, the absorbance at 225 nm is much more reduced, and it is apparent that dissolution of proteins and turbidity-increasing components is remarkably reduced in case of the product of the present invention.

EXAMPLE 5

The thickening effects of samples prepared in the same manner as described in Example 3 except that naphthenic acid was used instead of stearic acid were determined to obtain results shown in Table 4.

Table 4

| | (Thickening Effects) | | |
|---|---|---|---|
| Sample | Amount (g) of Naphthenic Acid | Amount (g) of Aluminum | Viscosity (cp) of Gelled Fuel Oil B |
| H | 1.5 | 0.59 | $4.0 \times 10^4$ |
| I | 3.0 | 0.60 | $5.0 \times 10^4$ |
| J | 6.0 | 0.62 | $4.2 \times 10^4$ |
| K | 9.0 | 0.65 | $2.8 \times 10^4$ |

As will be apparent from the results shown in Table 4, a highest thickening effect can be obtained when the amount of naphthenic acid is about ⅓ of the carboxymethylated crude product, and as the amount added of naphthenic acid is increased beyond this value, the thickening effect is rather reduced. In each sample, the aqueous phase was colorless and transparent.

EXAMPLE 6

Rosin was saponified with sodium carbonate or sodium hydroxide to obtain a rosin acid composed mainly of abietic acid. The thickening effects of samples prepared in the same manner as described in Example 3 except that the so prepared rosin acid was used instead of stearic acid were determined to obtain results shown in Table 5.

Table 5

| | (Thickening Effects) | | |
|---|---|---|---|
| Sample | Amount (g) of Rosin Acid | Amount (g) of Aluminum | Viscosity (cp) of Gelled Fuel Oil B |
| L | 1.7 | 0.58 | $6.0 \times 10^4$ |
| M | 3.4 | 0.60 | $8.0 \times 10^4$ |
| N | 5.1 | 0.61 | $9.4 \times 10^4$ |
| O | 6.8 | 0.62 | $12.2 \times 10^4$ |
| P | 8.5 | 0.63 | $10.5 \times 10^4$ |
| Q | 13.6 | 0.68 | $7.2 \times 10^4$ |
| R | 6.8 | 0 | $3.1 \times 10^4$ |

EXAMPLE 7

The thickening effects of samples prepared in the same prepared in the same manner as described in Example 3 except that a fatty acid indicated below was used instead of stearic acid were determined to obtain results shown in Table 6.

Table 6

| | (Thickening Effects) | | | |
|---|---|---|---|---|
| | Fatty Acid | | Amount | Viscosity (cp) |
| Sample | Kind | Amount (g) | (g) of Aluminum | of Gelled Fuel Oil B |
| S | caprylic acid | 1.5 | 0.66 | $1.9 \times 10^4$ |
| T | lauric acid | 1.5 | 0.63 | $2.7 \times 10^4$ |
| U | oleic acid | 1.5 | 0.61 | $1.9 \times 10^4$ |

As will be apparent from the results shown in Table 6, the thickening effect of lauric acid is higher than that of caprylic acid or oleic acid.

When the thickening effects of carboxylic acids are compared based on the results obtained in Examples 3 and 7 while the amount used of the carboxylic acid is kept constant, it is seen that the thickening effects are higher in the order of oleic acid ≈ caprylic acid < lauric acid < stearic acid, and that the thickening effect is higher as the molecular weight of the saturated fatty acid is increased and the thickening effect of the saturated fatty acid is higher than that of the unsaturated fatty acid. Similar tendencies are observed in alicyclic carboxylic acids.

EXAMPLE 8

In the foregoing Examples, the thickening effects of precipitation products obtained by adding a carboxylic acid to a crude carboxymethylation product of dry yeast cells and then adding a polyvalent metal salt in the presence of water were examined. In this Example, the thickening effects of compositions obtained by mixing a carboxymethylated product of a yeast with a polyvalent metal salt of a carboxylic acid were examined to obtain results shown in Table 7.

Table 7

| | (Thickening Effects) | | |
|---|---|---|---|
| | Fatty Acid Salt Added | | |
| Sample | Kind | Amount (g per 10 g of carboxymethylation product) | Viscosity (cp) of Gelled Fuel Oil B |
| V | aluminum stearate | 5 | $1.9 \times 10^4$ |
| W | aluminum stearate | 10 | $9.1 \times 10^4$ |
| X | calcium stearate | 5 | $1.5 \times 10^4$ |
| Y | calcium stearate | 10 | $1.8 \times 10^4$ |

From the results shown in Table 7, it is apparent that aluminum salts provide a higher thickening effect than calcium salts and aluminum salts are preferred as the polyvalent metal salt.

What is claimed is:

1. An oil coagulant comprising 100 parts by weight of a carboxymethyl yeast mixed with 10 to 150 parts by weight of a polyvalent metal salt of at least one carboxylic acid selected from the group consisting of a fatty acid having 8-22 carbon atoms and an alicyclic carboxylic acid having 8-22 carbon atoms.

2. An oil coagulant as set forth in claim 1 wherein 30 to 100 parts by weight of said polyvalent salt is incorporated into 100 parts by weight of the carboxymethylated yeast.

3. An oil coagulant as set forth in claim 1 wherein the yeast is a member selected from the group consisting of the genera Candida, Saccharomyces and Torula.

4. An oil coagulant as set forth in claim 3 wherein the yeast is one belonging to the species *Saccharomyces cerevisiae*.

5. An oil coagulant as set forth in claim 3 wherein the yeast is one belonging to the species *Torula utilis*.

6. An oil coagulant as set forth in claim 1 wherein the yeast is selected from the group consisting of yeasts belonging to the species *Candida utilis* and *Candida lipolytica*.

7. An oil coagulant as set forth in claim 1 wherein the higher fatty acid is a member selected from the group consisting of lauric acid, myristic acid, palmitic acid, stearic acid, behenic acid and mixtures thereof.

8. An oil coagulant as set forth in claim 7 wherein the higher fatty acid is stearic acid.

9. An oil coagulant as set forth in claim 1 wherein the alicyclic carboxylic acid is a member selected from the group consisting of naphthenic acids and rosin acids.

10. An oil coagulant as set forth in claim 1 wherein the polyvalent metal is a member selected from the group consisting of Mg, Ca, Ba, Al, Cu, Ni, Co, Mn, Zn, Pb, Cd, Ti, Cr, Fe, Ce and Zr.

11. An oil coagulant as set forth in claim 10 wherein the polyvalent metal is Al.

12. A process for the preparation of oil coagulants which comprises mixing with (A) a carboxymethylated yeast obtained by carboxymethylating yeast and then heating the carboxymethylated yeast at a temperature within a range of from 50° to 90° C. for 0.5 to 5 hours, either (B) a polyvalent metal salt of at least one carboxylic acid selected from the group consisting of a higher fatty acid having 8 to 22 carbon atoms and an an alicyclic carboxylic acid having 8 to 22 carbon atoms or (C) a mixture capable of forming a polyvalent metal salt of a carboxylic acid comprising at least one carboxylic acid selected from the group consisting of a higher fatty acid having 8 to 22 carbon atoms and an alicyclic carboxylic acid having 8 to 22 carbon atoms, an alkali metal salt, ammonium salt or organic basic salt of said carboxylic acid, and a water soluble polyvalent metal salt of an inorganic acid, in which said (B) polyvalent metal salt of carboxylic acid or said (C) mixture capable of forming a polyvalent metal salt of carboxylic acid is mixed with said (A) carboxymethylated yeast at a compound ratio such that the polyvalent metal salt of carboxylic acid is present in an amount within a range of 10 to 150 parts by weight to 100 parts by weight of said (A) carboxymethylated yeast.

13. A process for the preparation of oil coagulants according to claim 12 wherein the carboxymethylated yeast is heat-treated and then mixed with the metal salt of at least one member selected from the group consisting of higher fatty acids and alicyclic carboxylic acids.

14. A process for the preparation of oil coagulants according to claim 12 wherein the yeast is a member selected from the group consisting of the genera Candida, Saccharomyces and Torula.

15. A process for the preparation of oil coagulants according to claim 14 wherein the yeast is one belonging to the species *Torula utilis.*

16. A process for the preparation of oil coagulants according to claim 12 wherein the yeast is a member selected from the group consisting of the species *Candida utilis* and *Candida lipolytica.*

17. A process for the preparation of oil coagulants according to claim 12 wherein the yeast is one belonging to the species *Saccharomyces cerevisiae.*

18. A process for the preparation of oil coagulants according to claim 12 wherein the higher fatty acid is a member selected from the group consisting of lauric acid, myristic acid, palmitic acid, stearic acid, behenic acid and mixtures thereof.

19. A process for the preparation of oil coagulants according to claim 12 wherein the higher fatty acid is stearic acid.

20. A process for the preparation of oil coagulants according to claim 12 wherein the alicyclic carboxylic acid is a member selected from the group consisting of naphthenic acids and rosin acids.

21. A process for the preparation of oil coagulants according to claim 12 wherein the polyvalent metal of the polyvalent metal salt of the carboxylic acid is a member selected from the group consisting of Mg, Ca, Ba, Al, Cu, Ni, Co, Mn, Zn, Pb, Cd, Ti, Cr, Fe, Ce and Zr.

22. A process for the preparation of oil coagulants according to claim 12 wherein the polyvalent metal of the polyvalent metal salt of the carboxylic acid is Al.

23. A process for the preparation of oil coagulants according to claim 12 wherein at least two compounds capable of forming the metal salt of a member selected from the group consisting of higher fatty acids and alicyclic carboxylic acids by reaction thereof are at least one compound selected from the group consisting of higher fatty acids, alicyclic carboxylic acids and metal salts, ammonium salts and organic base salts of said carboxylic acids and a water-soluble polyvalent metal salt of an inorganic acid.

24. A process for the preparation of oil coagulants according to claim 12 wherein the salt of said carboxylic acid is an alkali metal salt of carboxylic acid.

25. A process for the preparation of oil coagulants according to claim 12 wherein the polyvalent metal of the polyvalent metal salt of the inorganic acid is a member selected from the group consisting of Mg, Ca, Ba, Al, Cu, Ni, Co, Mn, Zn, Pb, Cd, Ti, Cr, Fe, Ce and Zr.

26. A process for the preparation of oil coagulants according to claim 25 wherein the polyvalent metal is Al.

27. A process for the preparation of oil coagulants according to claim 12 wherein the inorganic acid is a member selected from the group consisting of sulfuric acid, hydrochloric acid and nitric acid.

28. A process for the preparation of oil coagulants according to claim 12 wherein the mixing together of the carboxymethylated yeast and the polyvalent metal salt of carboxylic acid or the mixture capable of forming the polyvalent metal salt of carboxylic acid is conducted in the presence of water.

29. A process for the preparation of oil coagulants which comprises mixing the (A) a carboxymethylated yeast obtained by carboxymethylating yeast either (B) a polyvalent metal salt of at least one carboxylic acid selected from the group consisting of a higher fatty acid having 8 to 22 carbon atoms and an alicyclic carboxylic acid having 8 to 22 carbon atoms or (C) a mixture capable of forming a polyvalent metal salt of carboxylic acid comprising at least one carboxylic acid selected from the group consisting of a fatty acid having 8 to 22 carbon atoms and an alicyclic carboxylic acid having 8 to 22 carbon atoms, an alkali metal salt, ammonium salt or organic basic salt of said carboxylic acid, and a water soluble polyvalent metal salt of an inorganic acid, in which said (B) polyvalent metal salt of a carboxylic acid or (C) mixture capable of forming a polyvalent metal salt of carboxylic acid is mixed with said (A) carboxymethylated yeast at a compound ratio such that the polyvalent metal salt of carboxylic acid is present in an amount within a range of from 10 to 150 parts by weight to 100 parts by weight of said (A) carboxymethylated yeast.

* * * * *